United States Patent [19]

Lindel et al.

[11] Patent Number: 4,845,262

[45] Date of Patent: Jul. 4, 1989

[54] NOVEL ARYLETHANOLAMINES FOR PROMOTING LIVESTOCK PRODUCTION

[75] Inventors: Hans Lindel, Leverkusen; Werner Hallenbach, Langenfeld; Friedrich Berschauer, Wuppertal; Anno de Jong, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 89,691

[22] Filed: Aug. 25, 1987

[30] Foreign Application Priority Data

Sep. 12, 1986 [DE] Fed. Rep. of Germany ....... 3631009

[51] Int. Cl.⁴ ............................................. A61K 31/135
[52] U.S. Cl. ..................... 558/415; 558/411; 558/431
[58] Field of Search ...................... 558/415, 411, 431

[56] References Cited

U.S. PATENT DOCUMENTS 4,404,222  9/1983  Baker .................................. 424/304

FOREIGN PATENT DOCUMENTS 26298   4/1981  European Pat. Off. .
0070133  1/1983  European Pat. Off. .
0170538  2/1986  European Pat. Off. .
2133986  8/1984  United Kingdom .

Primary Examiner—William R. Dixon, Jr.
Assistant Examiner—James M. Hunter, Jr.
Attorney, Agent, or Firm—Sprung, Horn, Kramer & Woods

[57] ABSTRACT

The growth of livestock is promoted by the novel arylethanolamines of the formula

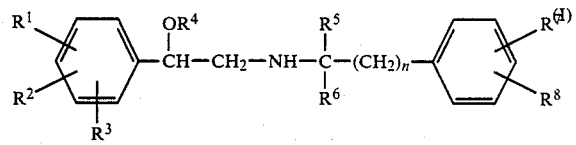

in which
$R^1$ represents cyano,
$R^2$ represents amino, alkylamino or acylamino,
$R^3$ represents hydrogen, halogen, alkyl, halogenoalkyl, alkoxy, halogenoalkoxy, hydroxymethyl, nitro or methylsulphonylmethyl,
$R^4$ represents hydrogen, alkyl or acyl,
$R^5$ represents hydrogen or alkyl,
$R^6$ represents alkyl,
n represents 1, 2 or 3,
$R^7$ represents the radicals $-COR^9$, $-O$-alkylene-$COR^9$, -alkylene-$R^{10}$ or $-O$-alkylene-$R^{10}$,
$R^8$ represents hydrogen, alkyl or halogen,
$R^9$ represents hydroxyl, alkoxy or the radical $-NR^{11}R^{12}$,
$R^{10}$ represents hydroxyl, alkoxy or the radical $NR^{11}R^{12}$,
$R^{11}$ represents hydrogen or alkyl, and
$R^{12}$ represents hydrogen or alkyl, and the physiologically acceptable salts thereof.

12 Claims, No Drawings

4,845,262

NOVEL ARYLETHANOLAMINES FOR PROMOTING LIVESTOCK PRODUCTION

SUMMARY OF THE INVENTION

The present invention relates to new arylethanolamines, processes for the preparation thereof, and the use thereof as production promoters for livestock.

Arylethanolamines are known compounds. Depending on their chemical structure, they have various pharmacological properties. Certain arylethanolamines have, inter alia, actions on the increase in weight of livestock and on the ratio between the formation of meat and fat (EP-OS (European Published Specification) No. 26,298). Here also, the basic structure of the arylethanolamine appears to be of decisive importance for the action.

The following have been found:
1. the new arylethanolamines of the formula I

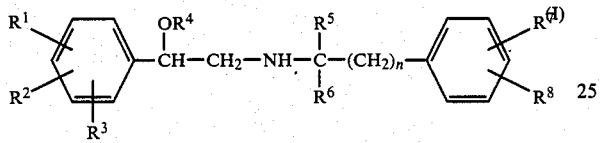

in which
$R^1$ represents cyano,
$R^2$ represents amino, alkylamino or acylamino,
$R^3$ represents hydrogen, halogen, alkyl, halogenoalkyl, alkoxy, halogenoalkoxy, hydroxymethyl, nitro or methylsulphonylmethyl,
$R^4$ represents hydrogen, alkyl or acyl,
$R^5$ represents hydrogen or alkyl,
$R^6$ represents alkyl,
n represents 1, 2 or 3,
$R^7$ represents the radicals —$COR^9$, —O-alkylene-$COR^9$, -alkylene-$R^{10}$ or —O-alkylene-$R^{10}$,
$R^8$ represents hydrogen, alkyl or halogen,
$R^9$ represents hydroxyl, alkoxy or the radical —$NR^{11}R^{12}$,
$R^{10}$ represents hydroxyl, alkoxy or the radical —$NR^{11}R^{12}$,
$R^{11}$ represents hydrogen or alkyl, and
$R^{12}$ represents hydrogen or alkyl,
and the physiologically acceptable salts thereof.

2. Processes for the preparation of compounds of the formula I

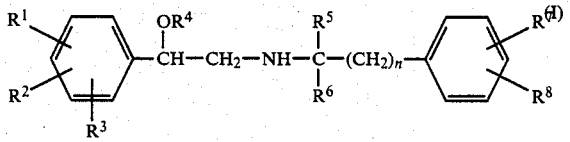

in which
$R^1$ represents cyano,
$R^2$ represents amino, alkylamino or acylamino,
$R^3$ represents hydrogen, halogen, alkyl, halogenoalkyl, alkoxy, halogenoalkoxy, hydroxymethyl, nitro or methylsulphonylmethyl,
$R^4$ represents hydrogen, alkyl or acyl,
$R^5$ represents hydrogen or alkyl,
$R^6$ represents alkyl,
n represents 1, 2 or 3,
$R^7$ represents the radicals —$COR^9$, —O-alkylene-$COR^9$, -alkylene-$R^{10}$ or —O-alkylene-$R^{10}$,
$R^8$ represents hydrogen, alkyl or halogen,
$R^9$ represents hydroxyl, alkoxy or the radical —$NR^{11}R^{12}$,
$R^{10}$ represents hydroxyl, alkoxy or the radical —$NR^{11}R^{12}$,
$R^{11}$ represents hydrogen or alkyl, and
$R^{12}$ represents hydrogen or alkyl,
characterized in that
(a) halogenomethyl ketones of the formula II

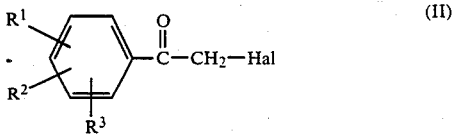

in which
$R^1$, $R^2$ and $R^3$ have the abovementioned meaning and Hal represents halogen,
are reacted with amines of the formula III

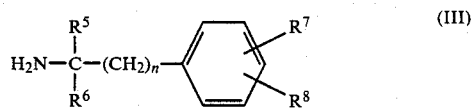

in which
$R^5$ to $R^8$ and n have the abovementioned meaning,
and the carbonyl group is subsequently reduced, or
(b) epoxides of the formula IV

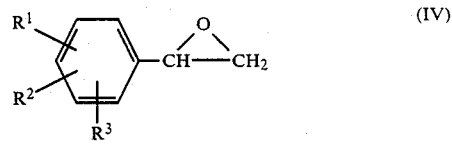

in which
$R^1$, $R^2$ and $R^3$ have the abovementioned meaning, are reacted with amines of the formula III

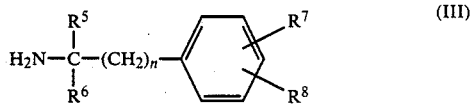

in which
$R^5$ to $R^8$ and n have the abovementioned meaning,
or
(c) β-halogenoethyl compounds of the formula V

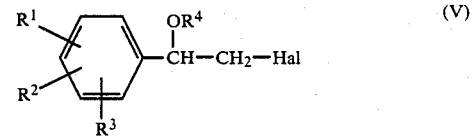

in which
$R^1$ to $R^4$ have the abovementioned meaning and Hal represents halogen,
are reacted with amines of the formula III

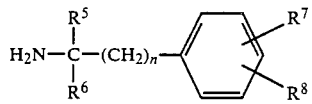

in which

R⁵ to R⁸ and n have the abovementioned meaning, or (d) in the case where, in formula I, R⁵ represents hydrogen, compounds of the formula VI

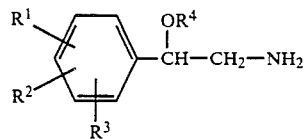

in which

R¹ to R⁴ have the abovementioned meaning, are reacted with compounds of the formula VII

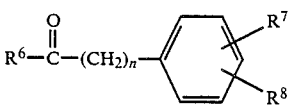

in which

R⁶, R⁷, R⁸ and n have the abovementioned meaning, under reducing conditions, or (e) compounds of the formula VIII

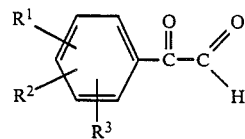

in which

R¹, R² and R³ have the abovementioned meaning, are reacted with amines of the formula III

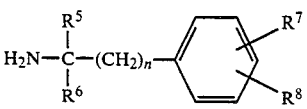

in which

R⁵ to R⁸ and n have the abovementioned meaning, under reducing conditions.

The compounds of the formula I can also exist in the form of their racemates and as mixtures of mutually diastereomeric or enantiomeric forms.

Physiologically acceptable salts of the compounds of the formula I can be formed with the following acids: hydrochloric acid, sulphuric acid, phosphoric acid, perchloric acid, hydrobromic acid, hydroiodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

DETAILED DESCRIPTION

Preferred compounds of the formula I are those in which $R^1$ represents cyano, $R^2$ represents amino, $C_1$-$C_3$-alkylamino or $C_1$-$C_3$-acylamino, $R^3$ represents hydrogen, halogen, halogenoalkyl or nitro, $R^4$ represents hydrogen, methyl, acetyl or benzoyl, $R^5$ represents hydrogen or $C_1$-$C_3$-alkyl, $R^6$ represents $C_1$-$C_3$-alkyl, n represents 1, 2 or 3, $R^7$ represents the radicals —$COR^9$, —O-alkylene-$COR^9$, -alkylene-$R^{10}$ or —O-alkylene-$R^{10}$, $R^8$ represents hydrogen, halogen or $C_1$-$C_3$-alkyl, $R^9$ represents hydroxyl, alkoxy or the radical $NR^{11}R^{12}$, $R^{10}$ represents hydroxyl, alkoxy or the radical $NR^{11}R^{12}$, $R^{11}$ represents hydrogen or $C_1$-$C_3$-alkyl and $R^{12}$ represents hydrogen or $C_1$-$C_3$-alkyl.

Particularly preferred compounds of the formula I are those in which $R^1$ represents cyano, $R^2$ represents amino, methylamino or acetylamino, $R^3$ represents hydrogen, fluorine, chlorine, bromine or trifluoromethyl, $R^4$ represents hydrogen or acetyl, $R^5$ represents hydrogen, $R^6$ represents methyl or ethyl, n represents 1 or 2, $R^7$ represents the radicals —$COR^9$, —O—$CH_2$—$COR^9$, —$CH_2$—$R^{10}$ or —O—$CH_2$—$CH_2$—$R^{10}$, $R^8$ represents hydrogen, chlorine or methyl, $R^9$ represents hydroxyl, $C_1$-$C_3$-alkoxy or the radical $NR^{11}R^{12}$, $R^{10}$ represents hydroxyl, methoxy or the radical $NR^{11}R^{12}$, $R^{11}$ represents hydrogen or methyl, and $R^{12}$ represents hydrogen or methyl.

Very particularly preferred compounds of the formula I are those in which $R^1$ represents cyano, $R^2$ represents amino, $R^3$ represents hydrogen or chlorine, $R^4$ represents hydrogen, $R^5$ represents hydrogen, $R^6$ represents methyl, n represents 1, $R^7$ represents the radicals —$COR^9$, —$OCH_2$—$COR^9$ or —O—$CH_2$—$CH_2R^{10}$, $R^8$ represents hydrogen, $R^9$ represents hydroxyl or methoxy, $R^{10}$ represents hydroxyl or the radical $NR^{11}R^{12}$, $R^{11}$ represents hydrogen, and $R^{12}$ represents hydrogen or methyl.

In addition to the examples, the following compounds of the formula I may be mentioned individually:

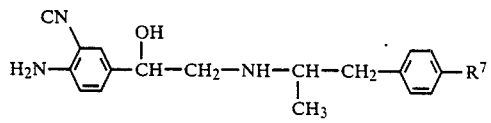

R⁷
OCH₂COOH
COOH

OCH₂CH₂NH₂
OCH₂CH₂NHCH₃

The salts with hydrochloric acid, sulphuric acid, phosphoric acid, oxalic acid, maleic acid, fumaric acid and malonic acid may preferably be mentioned.

The new compounds of the formula I can be prepared by the abovementioned processes 2(a) to (e).

In process 2(a), if 3-cyano-4-amino-5-chlorophenyl bromomethyl ketone is employed as halogenomethyl ketone of the formula II and 3-(4-carbomethoxyphenyl)-2-propylamine is employed as amine of the formula III, process 2(a) can be represented by the following equation:

3-(4-carboxyphenyl)-2-propylamine,
3-(4-carboxymethoxyphenyl)-2-propylamine,
3-(4-hydroxymethylphenyl)-2-propylamine,
3-(4-dimethylaminomethylphenyl)-2-propylamine, and
3-(4-(2-hydroxyethyl)phenyl)-2-propylamine.

The following reducing agents may be mentioned as reducing agents for carrying out process 2(a): H₂/catalyst, where the following may be mentioned as examples of catalyst: PtO₂ and Pd/activated charcoal; complex metal hydrides, such as, for example, LiAlH₄, NaBH₄ and NaBH₃CN.

The following reducing agents are particularly preferably employed: NaBH₄ and NaBH₃CN.

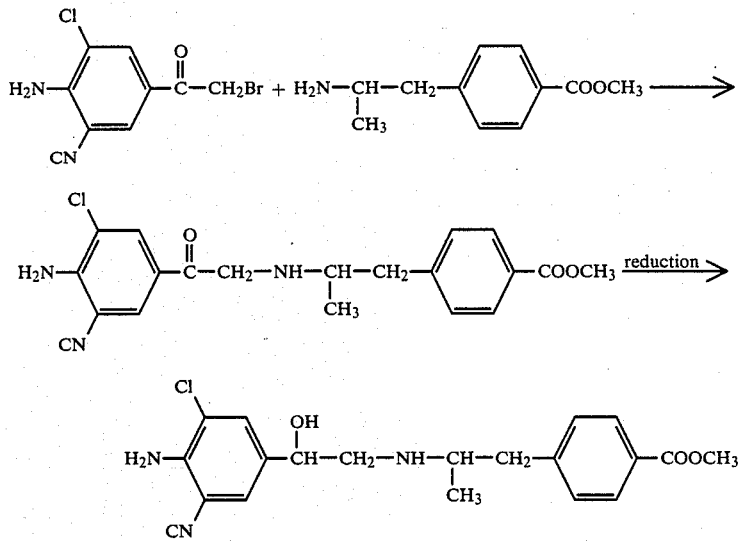

The compounds of the formula II are known (cf., for example, U.S. Pat. No. 4,404,222). The substituents R¹, R² and R³ preferably have the preferred meanings specified above in the case of the compounds of the formula I. The following compounds of the formula II may be mentioned individually:
3-cyano-4-aminophenyl bromomethyl ketone,
3-cyano-4-aminophenyl chloromethyl ketone,
3-cyano-4-amino-5-chlorophenyl bromomethyl ketone,
3-cyano-4-amino-5-trifluoromethylphenyl bromomethyl ketone,
3-cyano-4-acetaminophenyl chloromethyl ketone, and
3-cyano-4-methylamino-5-bromophenyl bromomethyl ketone.

The amines of the formula III are known (cf., for example, EP-OS (European Published Specification) No. 23,385). The substituents R⁵, R⁶, R⁷, R⁸ and n preferably have the preferred meanings specified above in the case of the compounds of the formula I. The following compounds of the formula III may be mentioned individually:
3-(4-carbomethoxyphenyl)-2-propylamine,
3-(4-methoxycarbonylmethoxyphenyl)-2-propylamine, Process 2(a) is carried out by mixing the compounds II and III in an approximately equimolar ratio in a diluent and subsequently reducing.

The reduction is preferably carried out at temperatures from −20° C. to +100° C.

The reduction is preferably carried out at atmospheric pressure.

The diluents are all inert organic solvents. These include, in particular, aliphatic and aromatic hydrocarbons, such as pentane, hexane, cyclohexane, petroleum ether, ligroin, benzene and toluene; chlorinated hydrocarbons, such as methylene chloride, ethylene chloride and chloroform; ethers, such as diethyl ether and glycol dimethyl ether; nitriles, such as acetonitrile, propionitrile and benzonitrile; and alcohols, such as methanol, ethanol and n- and i-propanol.

Alcohols are preferred, it being possible for the reduction to be carried out immediately without isolation of the intermediates.

In process 2(b), if (3-cyano-4-amino-5-chlorophenyl)ethylene oxide is employed as epoxide of the formula IV and if 3-(4-dimethylaminomethylphenyl)-2-propylamine is employed as amine of the formula III, process 2(b) can be represented by the following equation:

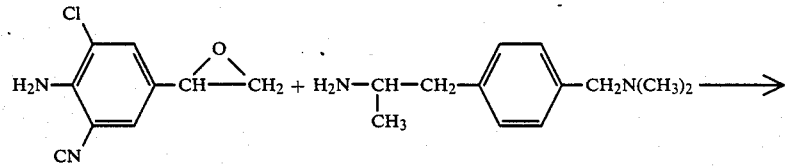

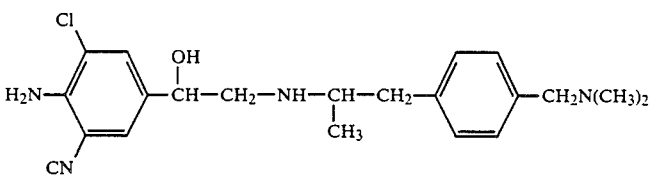

The epoxides of the formula V are known (cf., for example, U.S. Pat. No. 4,404,222). The substituents $R^1$, $R^2$ and $R^3$ preferably have the preferred meanings specified above in the case of the compounds of the formula I.

The following compounds of the formula IV may be mentioned individually:
(3-cyano-4-aminophenyl)-ethylene oxide,
(3-cyano-4-amino-5-chlorophenyl)-ethylene oxide,
(3-cyano-4-amino-5-trifluoromethylphenyl)-ethylene oxide, and
(3-cyano-4-methylaminophenyl)-ethylene oxide.

Process 2(b) is carried out by reacting approximately equimolar amounts of the epoxide of the formula IV and the amine of the formula III in a diluent.

In general, an excess of amine (1–3 molar, preferably 1–1.5 molar), relative to the epoxide of the formula IV, is used.

The reaction is carried out at temperatures from +20° to +150° C.

The reaction is preferably carried out at atmospheric pressure.

The diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, furthermore nitriles, such as acetonitrile and benzonitrile, amides, such as dimethylformamide, and alcohols, such as methanol, ethanol and n- and i-propanol.

Alcohols are preferred.

In process 2(c), if 1-(3-cyano-4-aminophenyl)-1-hydroxy-2-chloroethane is employed as β-halogenoethyl compound of the formula V and 3-(4-carbomethoxyphenyl)-2-propylamine is employed as amine of the formula III, process 2(c) can be represented by the following equation:

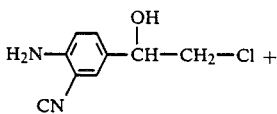

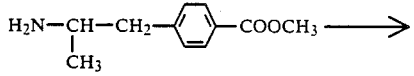

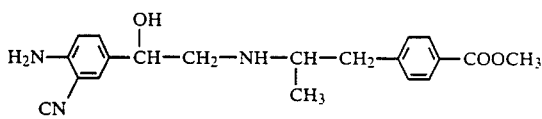

The β-halogenoethyl compounds of the formula V are known (cf., for example, U.S. Pat. No. 4,404,222). The substituents $R^1$ to $R^4$ preferably have the preferred meanings mentioned above in the case of the compounds of the formula I. The following compounds of the formula V may be mentioned individually:
1-(3-cyano-4-aminophenyl)-2-chloroethanol,
1-(3-cyano-4-aminophenyl)-2-bromoethanol,
1-(3-cyano-4-amino-5-chlorophenyl)-2-chloroethanol,
1-(3-cyano-4-amino-5-nitrophenyl)-2-chloroethanol,
1-(3-cyano-4-amino-5-nitrophenyl)-2-bromoethanol, and
1-(3-cyano-4-amino-5-trifluoromethylphenyl)-2-chloroethanol.

Process 2(c) is carried out by reacting the β-halogenoethyl compound of the formula V with excess amine of the formula III, if appropriate in the presence of a diluent.

The reaction is carried out at temperatures from +20° to +150° C.

The reaction is carried out at atmospheric pressure or under increased pressure.

The diluents are all inert organic solvents. These include, in particular, aliphatic and aromatic, optionally halogenated hydrocarbons, such as pentane, hexane, cyclohexane, benzene, toluene, methylene chloride and chloroform, furthermore ethers, such as diethyl ether, tetrahydrofuran and dioxane, in addition nitriles, such as acetonitrile, benzonitrile, furthermore amides, such as dimethylformamide, and furthermore alcohols, such as methanol, ethanol and n- and i-propanol.

Alcohols are preferably employed.

In process 2(d), if 1-(3-cyano-4-amino-5-chlorophenyl)-2-aminoethanol is employed as compound of the formula VI and 4-(dimethylaminomethyl)-phenylacetone is employed as compound of the formula VII, process 2(d) can be represented by the following reaction equation:

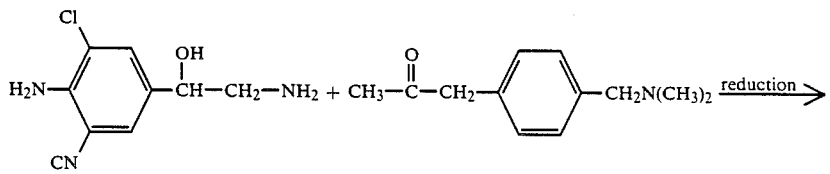

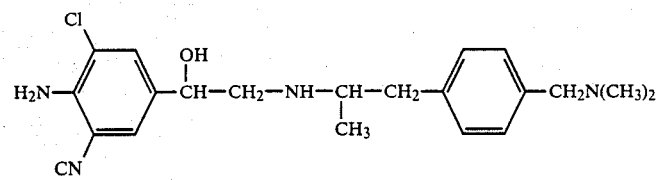

The compounds of the formula VI are known (cf., for example, U.S. Pat. No. 4,404,222). The substituents $R^1$ to $R^4$ preferably have the preferred meanings specified above in the case of the compounds of the formula I. The following compounds of the formula VI may be mentioned individually:
1-(3-cyano-4-aminophenyl)-2-aminoethanol,
1-(3-cyano-4-amino-5-bromophenyl)-2-aminoethanol,
1-(3-cyano-4-methylaminophenyl)-2-aminoethanol,
1-(3-cyano-4-amino-5-trifluoromethylphenyl)-2-aminoethanol.

The compounds of the formula VII are known (cf., for example, EP-OS (European Published Specification) No. 70,133). The substituents $R^6$ to $R^8$ and n preferably have the preferred meanings specified above in the case of the compounds of the formula I.

The following compounds of the formula VII may be mentioned individually:
4-carbomethoxyphenylacetone,
4-(carbomethoxymethoxy)phenylacetone and
4-(2-hydroxyethoxy)phenylacetone.

Process 2(d) is carried out by placing approximately equimolar amounts of the compounds of the formula VI and VII in a diluent and reducing the mixture.

The reaction is carried out at temperatures from 0° C. to 150° C.

The reaction is preferably carried out at atmospheric pressure.

The diluents are all inert organic solvents. These include aliphatic and aromatic, optionally halogenated hydrocarbons, such as pentane, hexane, cyclohexane, benzene, toluene, methylene chloride, ethylene chloride, chloroform and chlorobenzene, furthermore ethers, such as diethyl ether, tetrahydrofuran and dioxane, in addition nitriles, such as acetonitrile and benzonitrile, amides, such as dimethylformamide, and alcohols, such as methanol and ethanol.

The following are used as reducing agents: $H_2$/catalyst, where the catalyst may be, for example, $PtO_2$; and complex metal hydrides, such as, for example, $LiAlH_4$, $NaBH_4$ and $NaBH_3CN$.

In process 2(e), if 3-cyano-4-aminophenylglyoxal is used as compound of the formula VIII and 3-(4-methoxyphenyl)-2-propylamine is used as amine of the formula III, process 2(e) can be represented by the following reaction equation:

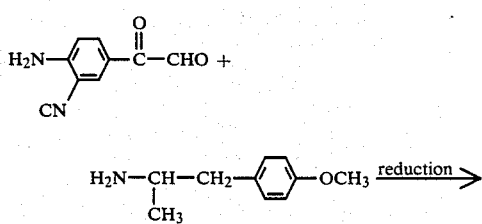

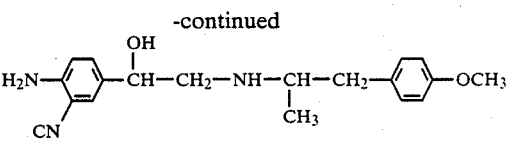

The compounds of the formula VIII are known (cf., for example, U.S. Pat. No. 4,404,222). The substituents $R^1$, $R^2$ and $R^3$ preferably have the preferred meanings mentioned above in the case of the compounds of the formula I. The following compounds of the formula VIII may be mentioned individually:
3-cyano-4-aminophenylglyoxal,
3-cyano-4-amino-5-chlorophenylglyoxal,
3-cyano-4-amino-5-bromophenylglyoxal, and
3-cyano-4-amino-5-trifluoromethylphenylglyoxal.

Process 2(e) is carried out by adding an approximately equivalent amount of the amine of the formula III to the compound of the formula VIII in a diluent, and subsequently reducing the mixture.

The reaction is carried out at temperatures from 0° C. to 100° C.

The reaction is preferably carried out at atmospheric pressure.

The diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, in addition esters, such as methyl acetate and ethyl acetate, furthermore nitriles, such as, for example, acetonitrile and propionitrile, benzonitrile and glutarodinitrile, in addition amides, such as, for example, dimethylformamide, dimethylacetamide and N-methylpyrrolidone, and also tetramethylene sulphone and hexamethylphosphoric triamide, and in addition alcohols, such as methanol, ethanol and n- and i-propanol.

The following are used as reducing agents: $H_2$/catalyst; where $PtO_2$ and Pd/charcoal may be mentioned as catalysts, and furthermore complex metal hydrides, such as $LiAlH_4$ and $NaBH_4$.

The active compounds are used as production promoters in livestock for promoting and accelerating growth and milk and wool production, for improving feed utilization and meat quality, and for shifting the meat/fat ratio in favor of the meat. The active compounds are used for commercial stock, breeding stock, ornamental stock and hobby stock.

The commercial and breeding stock include mammals, such as, for example, cattle, pigs, horses, sheep, goats, rabbits, hares, fallow deer, pelt animals such as mink and chinchilla, poultry, such as, for example, chickens, geese, ducks, turkeys and doves, fish, such as, for example, carp, trout, salmon, eels, tench and pike, and reptiles, such as, for example, snakes and crocodiles.

The ornamental and hobby stock include mammals, such as dogs and cats, birds, such as parrots and canaries, and fish, such as ornamental and aquarium fish, for example goldfish.

Irrespective of the sex of the livestock, the active compounds are employed in all growth and production phases of the livestock. The active compounds are preferably employed in the intensive growth and production phase. Depending on the type of livestock, the intensive growth and production phase lasts from one month to 10 years.

The amount of active compounds which is administered to the livestock in order to achieve the desired effect may be varied substantially as a result of the favourable properties of the active compounds. This amount is preferably about 0.001 to 50 mg/kg, particularly 0.01 to 5 mg/kg of body weight per day. The suitable amount of the active compound and the suitable duration of the administration depend, in particular, on the species, the age, the sex, the growth and production phase, the health and the type of keeping and feeding of the livestock, and can easily be determined by any expert.

The active compounds are administered to the livestock by conventional methods. The type of administration depends, in particular, on the species, the behavior and the health of the livestock.

The active compounds may be administered once. However, the active compounds may also be administered temporarily or continuously over the entire growth and production phase or over part of the growth and production phase.

In the case of continuous administration, administration can be carried out once or several times daily at regular or irregular intervals.

Administration is carried out orally or parenterally in formulations which are suitable for this or in pure form.

The active compounds may be present in the formulations alone or mixed with other production-promoting active compounds, mineral feedstuffs, trace element compounds, vitamins, non-protein compounds, colorants, antioxidants, aromas, emulsifiers, flow auxiliaries, preservatives and tabletting auxiliaries.

Other production-promoting active compounds are: for example, antibiotics, such as tylosin and virginamycin. Mineral feedstuffs are, for example, dicalcium phosphate, magnesium oxide and sodium chloride. Trace element compounds are, for example, iron fumarate, sodium iodide, cobalt chloride, copper sulphate and zinc oxide. Vitamins are, for example, vitamin A, vitamin $D_3$, vitamin E, B vitamins and vitamin C.

Non-protein compounds are, for example, biuret and urea. Colorants are, for example, carotinoids, such as citranaxanthin, zeaxanthin and capsanthin. Antioxidants are, for example, ethoxyquin and butylhydroxy-toluene. Aromas are, for example, vanillin. Emulsifiers are, for example, esters of lactic acid, and lecithin. Flow auxiliaries are, for example, sodium stearate and calcium stearate.

Preservatives, are for example, citric acid and propionic acid. Tabletting auxiliaries are, for example, ligninsulphonates and cellulose ethers.

The active compounds may also be administered together with the feed and/or with the drinking water.

The feed includes individual feedstuffs of vegetable origin, such as hay, beet and cereal by-products, individual feedstuffs of animal origin, such as meat, fats, milk products, bonemeal and fish products, individual feedstuffs such as vitamins, proteins, amino acids, for example DL-methionin, and salts such as lime and sodium chloride. The feed also includes supplementary feed, prepared feed and compound feed. These contain individual feedstuffs in a composition which ensures balanced nutrition with respect to the energy and protein supply and with respect to the supply of vitamins, mineral salts and trace elements.

The concentration of the active compounds in the feed is normally about 0.01–500 ppm, preferably 0.1–50 ppm.

The active compounds may be added to the feed as such or in the form of premixes or feed concentrates.

The following is an example of the composition of a feed for raising chicks which contains the active compound according to the invention:

200 g of wheat, 340 g of corn, 361 g of soybean meal, 60 g of beef fat, 15 g of dicalcium phosphate, 10 g of calcium carbonate, 4 g of iodinated common salt, 7.5 g of vitamin mineral mixture and 2.5 g of the active compound premix produce, after careful mixing, 1 kg of feed.

The following are contained in one kg of feed mixture: 600 I.U. of vitamin A, 100 I.U. of vitamin $D_3$, 10 mg of vitamin E, 1 mg of vitamin $K_3$, 3 mg of riboflavin, 2 mg of pyridoxin, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

2.5 g of active compound premix contain, for example, 10 mg of active compound, 1 g of DL-methionine, and the rest is soybean meal.

The following is an example of a composition of a feed for raising pigs which contains the active compound according to the invention:

630 g of feed-grain meal (composed of 200 g of corn, 150 g of barley meal, 150 g of oat meal and 130 g of wheat meal), 80 g of fish meal, 60 g of soybean meal, 60 g of tapioca meal, 38 g of brewer's yeast, 50 g of vitamin mineral mixture for pigs, 30 g of linseed cake meal, 30 g of corn gluten feed, 10 g of soy oil, 10 g of sugar cane molasses and 2 g of active compound premix (composition, for example, as in the case of chick feed) produce, after careful mixing, 1 kg of feed.

The feed mixtures mentioned are balanced for raising and fattening of, preferably, chicks or pigs, but they can also be used, in the same or a similar composition, for feeding other livestock.

EXAMPLE A

Rat feeding experiment

Female laboratory rats weighing 90–110 g of the SPF Wistar (Hagemann breed) type are fed ad lib with standard rat feed to which is added the desired amount of active compound. Each experimental group is carried out using feed from the identical batch, so that differences in the composition of the feed cannot impair the comparability of the results.

The rats receive water ad lib.

12 rats form each experimental group and are fed with feed to which the desired amount of active compound is added. A control group receives feed without active compound. The average body weight and the scattering in the body weights of the rats is the same in each experimental group, so that comparability of the experimental groups with one another is ensured.

During the 13-day experiment, the increase in weight and the consumption of feed are determined and the relative increase in weight compared to the untreated control is calculated.

The results which can be seen from the table are obtained:

| Rat-feeding experiment | | |
|---|---|---|
| Active compound (Ex. No.) | Dose 25 ppm | Relative increase in weight (%) |
| 1 | | 38 |
| 2 | | 33 |
| 3 | | 63 |
| 4 | | 32 |
| 5 | | 53 |

EXAMPLES

General procedure for process 2a

Preparation of the compounds of the formula I by process 2a 10 mmol of the compound of the formula II are added in portions to a solution of 10 mmol of the amine of the formula III in 15 ml of absolute ethanol at 0° C. The mixture is allowed to warm to 10°–15° C. and stirred at this temperature for a further hour. The mixture is then recooled to 0° C., and 600 mg (50 mmol) of sodium borohydride are added in portions. The mixture is stirred overnight at room temperature. After adding 20 ml of water, the mixture is stirred for 30 minutes, evaporated and distributed between water and ethyl acetate. The organic phase is dried over sodium sulphate and evaporated. The residue is recrystallized.

General procedure for process 2b

Preparation of the compounds of the formula I by process 2b 0.1 mol of the compound of the formula IV and 0.11 mol of the amine of the formula III are refluxed overnight in 200 ml of methanol. The solvent and excess amine are stripped off and the residue is recrystallized.

General procedure for process 2c

Preparation of the compounds of the formula I by process 2c 10 mmol of the compound of the formula V are dissolved in 150 ml of ethanol, 20 ml of the amine of the formula III are added, and the mixture is refluxed for 18 hours. The solvent and excess amine are then stripped off, and the residue is taken up in 100 ml of dry ether. The insoluble amine hydrohalide is filtered off, and the ethereal solution is washed with water, dried over sodium sulphate and evaporated. The crude product is recrystallized.

General procedure for process 2d

Preparation of the compounds of the formula I by process 2d 22 mmol of the carbonyl compound of the formula VII are added to 22 mmol of the compound VI in 10 ml of absolute ethanol at 0°–5° C. The mixture is allowed to warm to room temperature and stirred for a further 30 minutes. The solution is then added to 0.15 g of Adams catalyst (prehydrogenated in 10 ml of absolute ethanol), and the mixture is hydrogenated for 4–5 hours at 40° C. and a hydrogen pressure of 50 atm. After filtering off the catalyst, the filtrate is evaporated and the residue is recrystallized.

General procedure for process 2e

Preparation of the compounds of the formula I by process 2e 15 mmol of the amine of the formula III are added dropwise to a solution of 10 mmol of the compound of the formula VIII in 50 ml of ethanol at 10°–15° C. The mixture is allowed to warm to room temperature, and stirred for a further 15 minutes. The mixture is then diluted with a further 100 ml of ethanol, and 80 mmol of sodium borohydride are added in portions at 0°–5° C. The mixture is allowed to warm to room temperature and is stirred overnight. 200 ml of water are then added at 10° C., the mixture is stirred for 30 minutes, the ethanol is removed by evaporation, and the residue is extracted three times with 50 ml of dichloromethane in each case. The combined organic phases are washed with 100 ml of water, dried over sodium sulphate and evaporated.

The following compounds are prepared by the abovementioned processes 2(a) to 2(e):

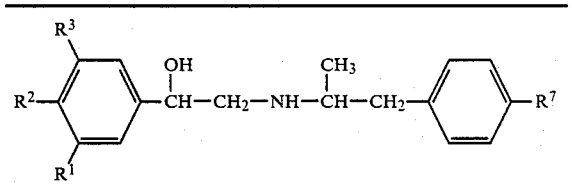

| Ex. No. | $R^1$ | $R^2$ | $R^3$ | $R^7$ | $^1$H NMR (DMSO—$d_6$, δ [(ppm)] |
|---|---|---|---|---|---|
| 1 | CN | $NH_2$ | H | $COOCH_3$ | 0.95 (d, 3H); 2.5–2.9 (m, 5H), 3.9 (s, 3H): 4.4 (m, 1H); 5.9 (s, 2H); 6.7 (d, 1H); 7.3 (m, 4H); 7.9 (m, 2H). |
| 2 | CN | $NH_2$ | H | $OCH_2CH_2OH$ | 0.9 (dd, 3H); 2.4–2.9 (m, 5H); 3.7 (m, 2H); 3.9 (m, 2H); 4.4 (m1H); 4.8 (s, 1H); 5.9 (s, 2H); 6.8 (m, 3H); 7.0 (m, 3H); 7.2 (m, 1H). |
| 3 | CN | $NH_2$ | H | $OCH_2COOCH_3$ | 0.9 (dd, 3H); 2.4–2.8 (m, 5H); 3.8 (2, 3H); 4.4 (s, 2H); 4.5 (m, 1H); 5.9 (s, 2H); 6.8 (m, 3H); 7.0–7.2 (m, 4H). |
| 4 | CN | $NH_2$ | Cl | $COOCH_3$ | 1.1 (d, 3H); 2.4–3.0 (m, 5H); 3.9 (s, 3H); 4.4 (m, 1H); 4.7 (s, 2H); 7.2 (m, 3H); 7.9 (m, 3H). |
| 5 | CN | $NH_2$ | Cl | $OCH_2COOCH_3$ | 1.1 (d, 3H); 2.4–3.0 (m, 5H); 3.8 (s, 3H); 4.5 (m, 1H); 4.6 (s, 2H); 4.8 (s,2H); 6.9 (m, 3H); 7.1 m (3H) |

It is understood that the specification and examples are illustrative but not limitative of the present invention and that other embodiments within the spirit and scope of the invention will suggest themselves to those skilled in the art.

We claim:

1. A member selected from the group consisting of an arylethanolamine of the formula

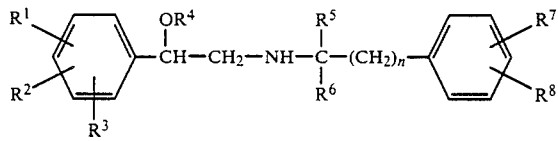

in which
R¹ represents cyano,
R² represents a member selected from the group consisting of amino, alkylamino and acylamino,
R³ represents a member selected from the group consisting of hydrogen, halogen, alkyl, halogenoalkyl, alkoxy, halogenoalkoxy, hydroxymethyl, nitro and methylsulphonylmethyl,
R⁴ represents a member selected from the group consisting of hydrogen, alkyl and acyl,
R⁵ represents a member selected from the group consisting of hydrogen and alkyl,
R⁶ represents alkyl,
n represents a member selected from the group consisting of 1, 2 and 3,
R⁷ represents a member selected from the group consisting of —COR⁹, —O—alkylene—COR⁹, —alkylene—R¹⁰ and —O—alkylene—R¹⁰,
R⁸ represents a member selected from the group consisting of hydrogen, alkyl and halogen,
R⁹ represents a member selected from the group consisting of hydroxyl, alkoxy and the radical —NR¹¹R¹²,
R¹⁰ represents a member selected from the group consisting of hydroxyl, alkoxy and the radical —NR¹¹R¹²,
R¹¹ represents a member selected from the group consisting of hydrogen and alkyl, and
R¹² represents a member selected from the group consisting of hydrogen and alkyl,
and a physiologically acceptable salt thereof.

2. A compound or salt according to claim 1, in which
R² represents a member selected from the group consisting of amino, C₁-C₃-alkylamino and C₁-C₃-acylamino,
R³ represents a member selected from the group consisting of hydrogen, halogen, halogenoalkyl and nitro,
R⁴ represents a member selected from the group consisting of hydrogen, methyl, acetyl and benzoyl,
R⁵ represents a member selected from the group consisting of hydrogen and C₁-C₃-alkyl,
R⁶ represents C₁-C₃-alkyl,
R⁸ represents a member selected from the group consisting of hydrogen, halogen and C₁-C₃-alkyl,
R¹¹ represents a member selected from the group consisting of hydrogen and C₁-C₃-alkyl and
R¹² represents a member selected from the group consisting of hydrogen and C₁-C₃-alkyl.

3. A compound or salt according to claim 1, in which
R¹ represents cyano,
R² represents a member selected from the group consisting of amino, methylamino and acetylamino,
R³ represents a member selected from the group consisting of hydrogen, fluorine, chlorine, bromine and trifluoromethyl,
R⁴ represents a member selected from the group consisting of hydrogen and acetyl,
R⁵ represents hydrogen,
R⁶ represents a member selected from the group consisting of methyl and ethyl, n represents a member selected from the group consisting of 1 and 2,
R⁷ represents a member selected from the group consisting of —COR⁹, —O—CH₂—COR⁹, —CH₂—R¹⁰ and —O—CH₂—CH₂—R¹⁰,
R⁸ represents a member selected from the group consisting of hydrogen, chlorine and methyl,
R⁹ represents a member selected from the group consisting of hydroxyl, C₁-C₃-alkoxy and the radical NR¹¹R¹²,
R¹⁰ represents a member selected from the group consisting of hydroxyl, methoxy and the radical NR¹¹R¹²,
R¹¹ represents a member selected from the group consisting of hydrogen and methyl, and
R¹² represents a member selected from the group consisting of hydrogen and methyl.

4. A compound or salt according to claim 1, in which
R¹ represents cyano,
R² represents amino,
R³ represents a member selected from the group consisting of hydrogen and chlorine,
R⁴ represents hydrogen,
R⁵ represents hydrogen,
R⁶ represents methyl,
n represents 1,
R⁷ represents a member selected from the group consisting of —COR⁹, —OCH₂—COR⁹ and —O—CH₂—CH₂—R¹⁰,
R⁸ represents hydrogen,
R⁹ represents a member selected from the group consisting of hydroxyl and methoxy,
R¹⁰ represents a member selected from the group consisting of hydroxyl and the radical NR¹¹R¹²,
R¹¹ represents hydrogen, and
R¹² represents a member selected from the group consisting of hydrogen and methyl.

5. A compound according to claim 1, wherein such compound is 1-hydroxy-1-(4-amino-3-cyano-phenyl)-2-(N-3-[4-carbomethoxyphenyl]-isopropylamino)-ethane of the formula

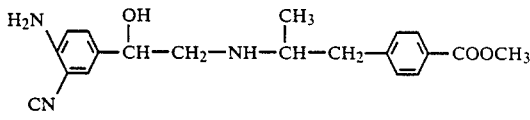

or a physiologically acceptable salt thereof.

6. A compound according to claim 1, wherein such compound is 1-hydroxy-1-(4-amino-3-cyano-phenyl)-2-(N-3-[4-hydroxyethoxyphenyl]-isopropylamino)-ethane of the formula

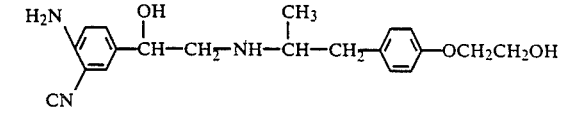

or a physiologically acceptable salt thereof.

7. A compound according to claim 1, wherein such compound is 1-hydroxy-1-(4-amino-3-cyano-phenyl)-2-(N-3-[4-carbomethoxymethoxyphenyl]-isopropylamino)-ethane of the formula

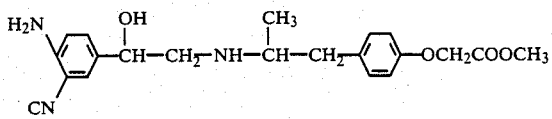

or a physiologically acceptable salt thereof.

8. A compound according to claim 1, wherein such compound is 1-hydroxy-1-(4-amino-5-chloro-3-cyano-phenyl)-2-(N-3-[4-carbomethoxyphenyl]-isopropylamino)-ethane of the formula

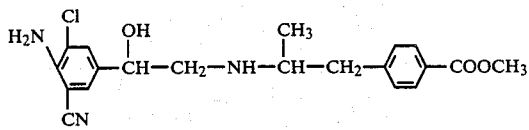

or a physiologically acceptable salt thereof.

9. A compound according to claim 1, wherein such compound is 1-hydroxy-1-(4-amino-5-chloro-3-cyano-phenyl)-2-(N-carbomethoxymethoxyphenyl]-isopropylamino)-ethane of the formula

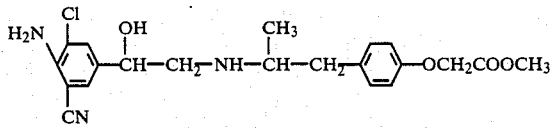

or a physiologically acceptable salt thereof.

10. A livestock growth-promoting composition comprising an amount effective therefor of a compound or salt according to claim 1 and an edible diluent.

11. A method of promoting the growth of livestock which comprises applying to such livestock a growth promoting effective amount of a member selected from the group consisting of an arylethanolamine of the formula

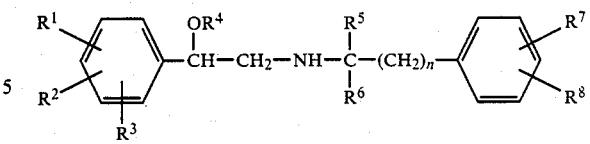

in which
$R^1$ represents cyano,
$R^2$ represents a member selected from the group consisting of amino, alkylamino and acylamino,
$R^3$ represents a member selected from the group consisting of hydrogen, halogen, alkyl, halogenoalkyl, alkoxy, halogenoalkoxy, hydroxymethyl, nitro and methylsulphonylmethyl,
$R^4$ represents a member selected from the group consisting of hydrogen, alkyl and acyl,
$R^5$ represents a member selected from the group consisting of hydrogen and alkyl,
$R^6$ represents alkyl,
n represents a member selected from the group consisting of 1, 2 and 3,
$R^7$ represents a member selected from the group consisting of —$COR^9$, —O—alkylene—$COR^9$, —alkylene—$R^{10}$ and —O—alkylene—$R^{10}$,
$R^8$ represents a member selected from the group consisting of hydrogen, alkyl and halogen,
$R^9$ represents a member selected from the group consisting of hydroxyl, alkoxy and the radical —$NR^{11}R^{12}$,
$R^{10}$ represents a member selected from the group consisting of hydroxyl, alkoxy and the radical —$NR^{11}R^{12}$,
$R^{11}$ represents a member selected from the group consisting of hydrogen and alkyl, and
$R^{12}$ represents a member selected from the group consisting of hydrogen and alkyl,
and a physiologically acceptable salt thereof.

12. The method according to claim 11, wherein such compound is
1-hydroxy-1-(4-amino-3-cyano-phenyl)-2-(N-3-[4-carbomethoxyphenyl]-isopropylamino)-ethane,
1-hydroxy-1-(4-amino-3-cyano-phenyl)-2-(N-3-[4-hydroxyethoxyphenyl]-isopropylamino)-ethane,
1-hydroxy-1-(4-amino-3-cyano-phenyl)-2-(N-3-[4-carbomethoxymethoxyphenyl]-isopropylamino)-ethane,
1-hydroxy-1-(4-amino-5-chloro-3-cyano-phenyl)-2-(N-3-[4-carbomethoxyphenyl]-isopropylamino)-ethane or
1-hydroxy-1-(4-amino-5-chloro-3-cyano-phenyl)-2-(N-carbomethoxymethoxyphenyl]-isopropylamino)-ethane,
or a physiologically acceptable salt thereof.

* * * * *

UNITED STATES PATENT AND TRADEMARK OFFICE
CERTIFICATE OF CORRECTION

PATENT NO. : 4,845,262

DATED : July 4, 1989

INVENTOR(S) : Lindel et al.

It is certified that error appears in the above-identified patent and that said Letters Patent is hereby corrected as shown below:

Title Page, ABSTRACT: After "formula" add --I--, in formula

Col 1, line 22 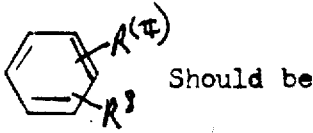 Should be 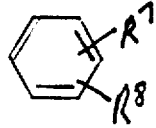

Col. 1, line 53 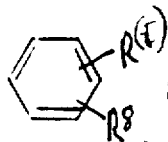 Should be 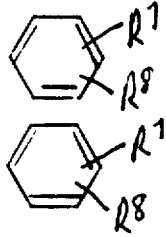

Col. 14, line 48  Should be

Col. 14, line 48  Example No. 3 under $^1$H NMR (DMSO-d$_6$ $\delta$(ppm))
after "3.8" delete "(2,3H)" and substitute --(S,3H)--

Signed and Sealed this

Sixteenth Day of April, 1991

Attest:

HARRY F. MANBECK, JR.

Attesting Officer

Commissioner of Patents and Trademarks